(12) United States Patent
Bruce et al.

(10) Patent No.: US 6,714,294 B1
(45) Date of Patent: Mar. 30, 2004

(54) DE BROGLIE MICROSCOPE

(75) Inventors: Michael R. Bruce, Austin, TX (US);
Victoria Jean Bruce, Austin, TX (US);
Rama R. Goruganthu, Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/209,844

(22) Filed: Jul. 31, 2002

(51) Int. Cl.$^7$ ............................................. G01N 21/00
(52) U.S. Cl. .................................................. 356/237.1
(58) Field of Search .......................... 356/237.1–237.5; 250/559.11, 559.13, 559.22, 559.34, 559.4, 559.41

(56) References Cited

U.S. PATENT DOCUMENTS

| | | | | |
|---|---|---|---|---|
| 5,574,276 A | * | 11/1996 | Ishimaru | 250/222.2 |
| 6,046,802 A | * | 4/2000 | Ortiz, Jr. | 356/237.1 |
| 6,208,750 B1 | * | 3/2001 | Tsadka | 382/145 |

OTHER PUBLICATIONS

A. Einstein et al.; *Can Quantum–Mechanical Description of Physical Reality Be Considered Complete*; Physical Review, vol. 47; May 1935; pp. 777–780.

Alain Aspect et al.; *Experimental Realization of Einstein–Podolsky–Rosen–Blhm Gedankenexperiment: A New Violoation of Bell's Inequalities*; Physical Review Letters, vol. 49, No. 2; Jul. 12, 1982; pp. 91–94.

J. Mertz et al.; *Single–molecule detection by two–photon–excited fluorescence*, Optics Letters, vol. 20, No. 24; Dec. 15, 1995; pp. 2532–2534.

Cern Courier; *Fresnel plate sharpens focus of heliumbeam*; http://www.cerncourier.com/main/article/40/2/10; 1998; pp. all.

Timothy E. Keller et al.; *Theory of the three–photon entangled state*; Physical Review A, vol. 57, No. 3; Mar. 1998; pp. 2076–2079.

Jan Perina, Jr. et al.; *Multiphoton absorption cross section and virtual–state spectroscopy for the entangled n–photon state*; Physical Review A, vol. 57, No. 5; May 1998; pp. 3972–3986.

E. J. S. Fonseca et al.; *Measurement of the de Broglie Wavelength of a Multiphoton Wave Packet*; Physical Review Letters, vol. 82, No. 14; Apr. 5, 1999; pp. 2868–2871.

Paul G. Kwiat et al.; *Ultrabright source of polarization–entangled photons*; Physical Review A, vol. 60, No. 2; Aug. 1999; pp. R773–R776.

Agedi N. Boto et al.; *Quantum Interferometric Optical Lithography; Exploiting Entanglement to Beat the Diffraction Limit*; Physical Review Letters; vol. 85, No. 13; Sep. 25, 2000; pp. 2733–2736.

E. J. S. Fonseca et al.; *Non–local de Broglie wavelength of a two–particle system*; Physical Review A, vol. 63, No. 043819; 2001; pp. 1–5.

Milena D'Angelo et al.; *Two–Photon Diffraction and Quantum Lithography*; Physical Review Letters, vol. 87, No. 1; Jul. 2, 2001; pp. 1–4.

Max Born et al.; *Principles of Optics*, 6th (corrected) Edition, 1980 and 1986; pp. 333–337.

Jungsang Kim et al.; *Entangled Electrons and Photons*; http://feynman.stanford.edu/Web/Main.htm; Jul. 2002; pp. 1–2.

Milan R. Pavlovic; *De Broglie's Perpetual Motion*; http://users.net.yu/~mrp/chapter26.html; Apr. 2002; pp. 1–3.

\* cited by examiner

*Primary Examiner*—Michael P. Stafira
(74) *Attorney, Agent, or Firm*—Timothy M. Honeycutt

(57) ABSTRACT

Methods and apparatus for inspecting a sample are provided. In one aspect, a method of inspection is provided that includes generating an entangled set of particle beams and directing one of the entangled set of particle beams to a location of a workpiece. One of the entangled set of particle beams interacts with the location of the workpiece. One of the entangled set of particle beams is observed after the interaction with the location of the workpiece to inspect the location of the workpiece.

49 Claims, 2 Drawing Sheets

DE BROGLIE MICROSCOPE

BACKGROUND OF THE INVENTION

1. Field of the Invention

This invention relates generally to semiconductor processing, and more particularly to an apparatus for and method of inspection using entangled particle beams.

2. Description of the Related Art

Accurate and reliable defect inspection is vital to successful semiconductor fabrication. Microelectronic circuit structures may be highly sensitive to perturbations in the myriad of process steps that must be performed in their fabrication. For example, particulate contamination introduced by various semiconductor processing tools and unwanted residual films left over after various semiconductor processing steps can lead to device performance issues or require wafer scrap. Most semiconductor chip fabrication techniques involve the sequential application of films of various composition on a silicon wafer or substrate. The successful application of the various films on top of each other often requires a relatively pristine underlying surface upon which the next formed layer is formed. However, the presence of an unwanted residual film on the underlying layer may cause the overlying film to later delaminate and lead to device failure.

Conventional optical microscopy as a means of inspection is rapidly approaching the available limits of resolution for microelectronic devices. Conventional means of improving resolution including obtaining a higher numerical aperture, and shorter light wavelengths must still address diffraction limits as well as the high cost of larger lenses and higher frequency light sources for such upgraded imaging systems. For example, if it is desired to use light below a wavelength of about 180 nm, then complex vacuum systems must typically be employed since air does not transmit light well at wavelengths below 180 nm.

Another conventional means of optical imaging for microelectronic structures involves near field scanning optical microscopy ("NSOM"). NSOM systems can achieve high resolution but at the expense of a very small field of view since the probe tip for such systems entail a very small aperture that is placed extremely close to the surface to be imaged. These types of NSOM systems are typically not practical for most finished integrated circuits where the layer of interest to be imaged may be buried under a passivation layer or a substrate in the case of back side imaging.

The present invention is directed to overcoming or reducing the effects of one or more of the foregoing disadvantages.

SUMMARY OF THE INVENTION

In accordance with one aspect of the present invention, a method of inspection is provided that includes generating an entangled set of particle beams and directing one of the entangled set of particle beams to a location of a workpiece. One of the entangled set of particle beams interacts with the location of the workpiece. One of the entangled set of particle beams is observed after the interaction with the location of the workpiece to inspect the location of the workpiece.

In accordance with another aspect of the present invention, a method of inspection is provided that includes generating a plurality of pairs of entangled photons. The plurality of pairs of entangled photons is divided into a first beam and a second beam. One of the first and second beams is directed to a location of a workpiece such that it interacts with the location of the workpiece. One of the first and second beams is observed after the interaction with the location of the workpiece to inspect the location of the workpiece.

In accordance with another aspect of the present invention, an inspection device is provided that includes a radiation source capable of transmitting an incident beam, a nonlinear member for producing a set of entangled beams from the incident beam, and an imaging device for observing an interaction of one of the set of entangled beams with a location of a workpiece.

In accordance with another aspect of the present invention, an inspection device is provided that includes a radiation source capable of transmitting an incident beam and a nonlinear crystal for producing a plurality of pairs of entangled photons from the incident beam. The plurality of pairs of entangled photons is divided into a first beam and a second beam. An imaging device is provided for observing an interaction of one of the first and second beams with a location of a semiconductor workpiece.

BRIEF DESCRIPTION OF THE DRAWINGS

The foregoing and other advantages of the invention will become apparent upon reading the following detailed description and upon reference to the drawings in which.

DESCRIPTION OF SPECIFIC EMBODIMENTS

Figure 1:
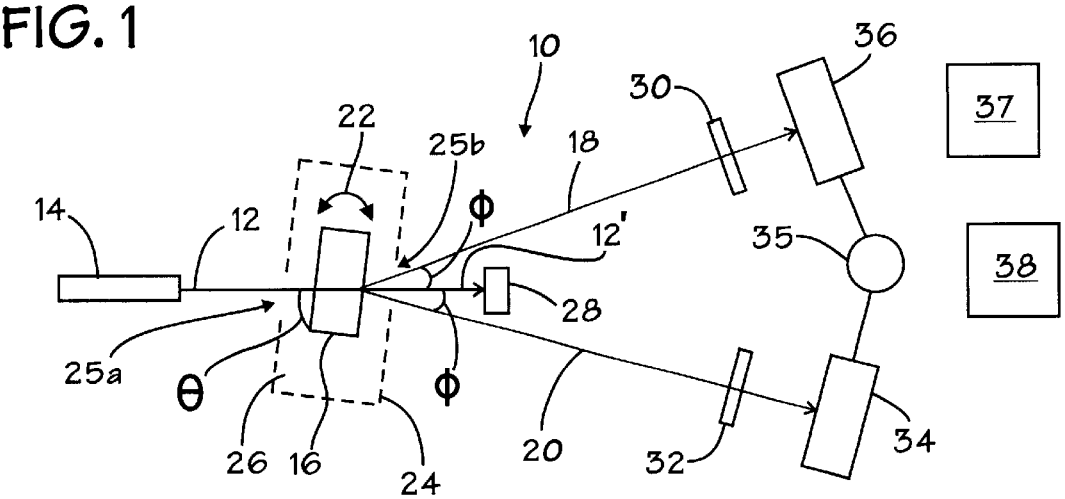
FIG. 1 is a schematic view of an exemplary embodiment of a quantum imaging system that utilizes sets of entangled particles in order to directly or indirectly image a sample in accordance with the present invention.

In the drawings described below, reference numerals are generally repeated where identical elements appear in more than one figure. Turning now to the drawings, and in particular to FIG. 1, therein is shown a schematic view of an exemplary embodiment of a quantum imaging system 10 that utilizes sets of entangled particles in order to directly or indirectly image a sample. An incident beam 12 of wavelength A is propagated by a radiation source 14. The incident beam 12 is passed through a member 16 that is capable of parametric down conversion such that a set of entangled particle beams is generated. In the illustrated embodiment, a pair of entangled beams 18 and 20 emanates from the nonlinear member 16. The entangled beams 18 and 20 may consist of a single pair of entangled particles or a plurality of pairs of entangled particles depending upon the output of the radiation source 14. The beams themselves 18 and 20 may consist of photons or other particles, such as, for example, electrons as desired. In the illustrative embodiment, the entangled beams 18 and 20 consist of one or more pairs of entangled photons.

The quantum process of entanglement by means of parametric down conversion results in the entangled beams 18 and 20 each having a wavelength a. However, the entangled nature of the beams 18 and 20 is such that each beam 18 and 20 has the effective resolution of the incident beam 12, that is, $\lambda$. In this way, the entangled beams 18 and 20 may have a wavelength that provides desirable optical transmission properties without sacrificing resolution. For example, silicon does not transmit light well at wavelengths below about 1.0 $\mu$m, but does transmit light well at around 1.0 $\mu$m. Using the present invention, the incident beam 12 may have a wavelength $\lambda$ of 0.5 $\mu$m and the entangled beams 18 and 20 may have a wavelength of 1.0 $\mu$m, which not only provides excellent transmission in silicon but also a desirable effective resolution of 0.5 $\mu$m. These wavelengths are merely illustrative.

The parametric down conversion of the incident beam 12 is accomplished via the nonlinear member 16. The nonlinear member 16 is capable of frequency mixing the incoming beam 12 to produce the entangled split-particle beams 18 and 20. In an exemplary embodiment, the member 16 consists of a nonlinear crystal. A variety of nonlinear crystal materials maybe used. In the illustrated embodiment, the member 16 is composed of beta barium borate ("BBO"). The width of the member 16 should be at least as large as the width of the incident beam 12. For example, an exemplary member 16 may have a width of about 1 cm. Many types of commercial BBO crystals are fabricated as a cube with two or more facets having the same dimension.

The non-linear member 16 should be pivotable about an axis projecting out of the drawing sheet as indicated by the arrows 22. In this way, the nonlinear member 16 may be pivoted to adjust the angle of incidence $\theta$ of the incident beam 12 until the desired production of the entangled beams 18 and 20 occurs, or completely detuned so that no parametric down conversion occurs. This tuning of the orientation of the nonlinear member 16 may be performed manually or in an automated fashion as desired. The nonlinear member 16 may be housed in a housing 24, shown in dashed. The housing 24 is provided with an inlet window 25a and an exit window 25b to enable the incident beam 12 to enter and the entangled beams 18 and 20 to exit the housing 24. The windows 25a and 25b should be composed of a material that is optically transparent at the frequencies of the incident beam 12 and the entangled beams 18 and 20. For example, the windows 25a and 25b may be composed of borophosphosilicate glass for radiation in the infrared region, or quartz, sapphire or magnesium chloride for higher frequencies.

Index phase matching may be provided by a suitable index phase matching fluid 26 in the housing 24. The index phase matching fluid should fully immerse the portion of the nonlinear member encompassing the travel path of the incident beam 12. Well-known index phase matching fluids, such as those produced by Cargil, may be used.

Note that the entangled beams 18 and 20 transmit away from the nonlinear member 16 at an angle 4 with respect to the incident beam 12. The magnitude of the angle $\phi$ will depend upon parameters such as the wavelength of the incident beam 12, the nonlinear properties of the member 16 and the angle of incidence $\theta$. Some of the incident beam 12 passes directly through the nonlinear member 16 as shown by the ray 12'. This beam 12' is advantageously blocked or absorbed by a beam dump 28. In order to further isolate the entangled beams 18 and 20 from noise radiation, filters 30 and 32 are positioned in the paths of the entangled beams 18 and 20 to filter out radiation at wavelength $\lambda$. A coincidence counter 35 of well-known design may be provided to verify the temporal alignment of the beams 18 and 20.

One of the entangled beams 18 or 20 is delivered to an imaging system 34 and the other is delivered to a detector 36. In the illustrated embodiment, the entangled beam 18 is transmitted to the detector 36 and the entangled beam 20 is transmitted to the imaging system 34. A process control system 37 may be provided and interfaced with the imaging system 10. The process control system 10 may be a computer or other automated device capable of controlling semiconductor fabrication tools and the movements of workpieces between such tools. One such tool is shown and designated 38. The tool 38 may be any of a myriad of devices in semiconductor fabrication, such as, for example, an etch tool, an inspection tool, a film deposition tool, a measurement tool, or a cleaning tool, to name to just a few. Following inspection in the imaging system 10, a workpiece or sample may be undergo further processing as necessary in, for example, the tool 38 and/or other tools or devices. Furthermore, information obtained from the imaging system 10 may be delivered or fed back to the process control system 37 for use elsewhere or to the tool 38 or both. In either case, the information obtained from the inspection in the imaging system 10 may be used to modify, if necessary, operations on other workpieces or samples.

Figure 2:
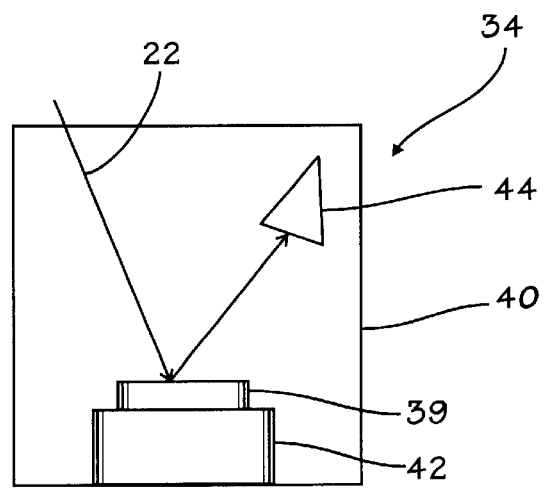
FIG. 2 is a schematic view of an exemplary embodiment of an imaging system that may be used with the imaging system of FIG. 1 in accordance with the present invention.

The entangled beam 20 may be used as an illumination source for the imaging system 34 in at least two modes of operation for the imaging system 34. In a first or reflectance mode of operation depicted in FIG. 2, the entangled beam 20 is used to illuminate a sample or workpiece 39 that is positioned within a housing 40 and on a stage or holder 42 of conventional well-known design. The purpose of the housing 40 is to block out unwanted radiation that might otherwise obscure the imaging. The workpiece 39 maybe a semiconductor wafer, or virtually any other object that may benefit from microscopic imaging. The entangled beam strikes 20 the workpiece 39 and reflects upward toward an imaging device 44, which may be, for example, a scanning laser microscope, an optical microscope, or other type of imaging device. The entangled nature of the beam 20 due to parametric down conversion results in the beam 20 propagating at a wavelength 2$\lambda$ but with an effective resolution of $\lambda$.

Figure 3:
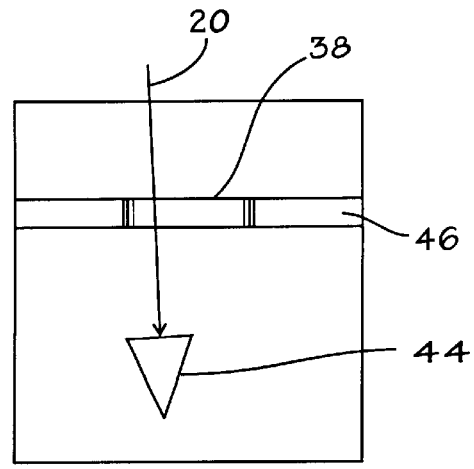
FIG. 3 is a schematic view of an alternate exemplary embodiment of an imaging system that may be used with the imaging system of FIG. 1 in accordance with the present invention.

In an alternate embodiment, the imaging system 34 may be operated in a transmission mode as shown in FIG. 3. In this embodiment, the workpiece 39 is positioned in the housing 40 and supported by a carrier 46 such that the entangled beam 20 may pass through the workpiece 39 and be sensed in a transmission mode by the imaging device 44. Again, the beam 20 provides for a doubling of wavelength without sacrificing resolution.

Referring again to FIG. 1, the detector 36 may be configured as a simple radiation detector to sense the presence of the entangled beam 18 and thereby ensure that the incident beam 12 is indeed parametrically down-converted to two entangled beams 18 and 20 as desired. Optionally, the detector 36 may be configured to act as more than merely a detector of incoming photons. Rather, the detector 36 may be configured to perceive the image that is being projected to the imaging device 44 in the imaging system 34. As the skilled artisan will appreciate, the behavior of the entangled beam 20 is mimicked by the entangled beam 18. Thus, the detector 36 may be used as a way of verifying the image picked up by the imaging device 34.

Figure 4:
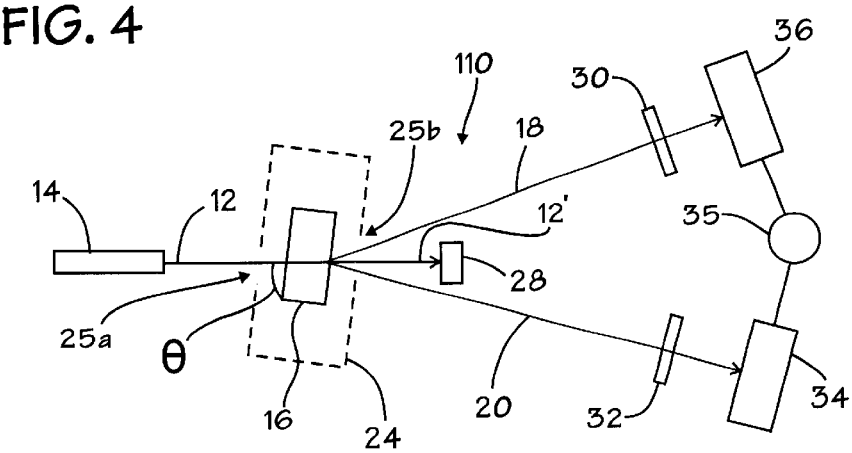
FIG. 4 is a schematic view of an alternate exemplary embodiment of a quantum imaging system that utilizes sets of entangled particles in order to directly or indirectly image a sample in accordance with the present invention.
Figure 5:
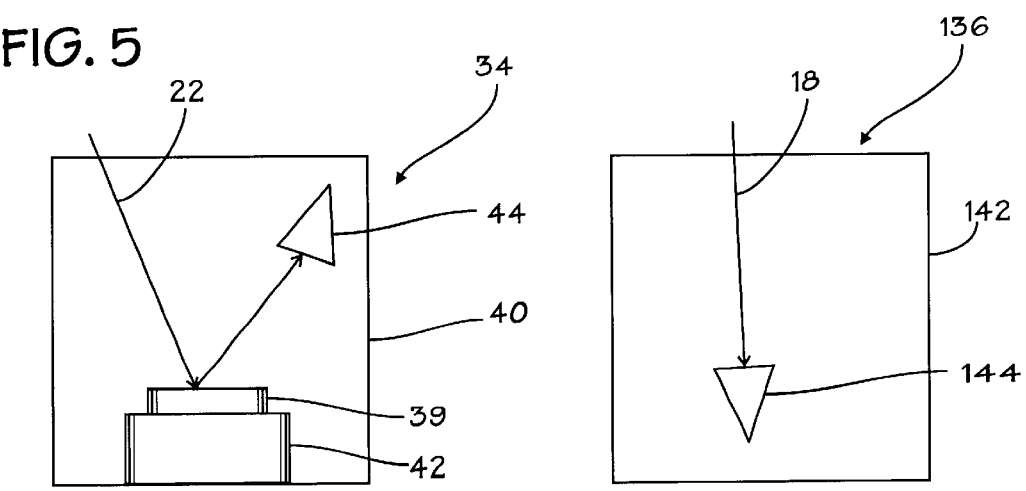
FIG. 5 is a schematic view of an exemplary embodiment of an imaging system that may be used with the imaging system of FIG. 4 in order to remotely observe a sample in accordance with the present invention.

The entanglement properties of the entangled beams 18 and 20 maybe used to remotely sense or image the features of the workpiece 39. An illustrative embodiment incorporating this remote sensing feature is shown in FIGS. 4 and 5. FIG. 4 is a schematic view like FIG. 1. Like the embodiment disclosed elsewhere herein, the quantum imaging system 110 utilizes an incident beam 12 from the radiation source 14. The incident beam 12 is transmitted to the nonlinear member 16 through the window 25a in the housing 24 at an angle θ. The beam 12 is parametrically down-converted such that a set of entangled particle beams 18 and 20 is generated that exits the window 25b. The transmitted portion 12' of the beam is absorbed in the dump 28. Filters 30 and 32 and a coincidence counter 35 are provided as described elsewhere herein. In this illustrative embodiment, the entangled beam 20 is again used to illuminate the workpiece 39 positioned on a carrier 42 in the housing 40. However, the use of an imaging device 44 for inspecting the workpiece 39 directly is optional. Instead, and as shown in FIG. 5, a detector 136 may be configured with an imaging device 144 that can image the workpiece 39 by actually imaging the entangled beam 18. As noted above, since the beams 18 and 20 are entangled in the quantum sense, the behavior of the entangled beam 20 may be observed by observing the entangled beam 18.

The foregoing exemplary embodiments are described in the context of two entangled beams. However, the skilled artisan will appreciate that greater than two entanglements may be utilized. For example, N entangled beams may be used and generated by, for example, pumping incident radiation into a nonlinear member that has $X^{(N)}$ nonlinear susceptibility. Another option involves utilizing a nonlinear member consisting of a cascade of N−1 nonlinear members each having $\chi^{(2)}$ nonlinear susceptibility to produce N entangled beams. The incident beam is pumped into the first nonlinear member to produce two entangled beams. One of these entangled beams is then passed into the next nonlinear member to generate two more entangled beams, and so on for the remaining nonlinear members.

Figure 6:
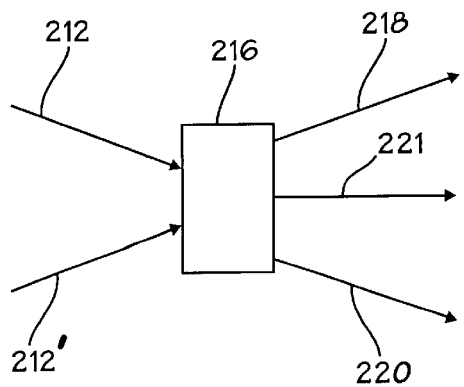
FIG. 6 is a schematic view of another alternate exemplary embodiment of a quantum imaging system in accordance with the present invention.

In yet another alternative, parametric down conversion may be combined with sum frequency generation to produce an entangled three-photon state that yields an increase in resolution. An exemplary apparatus 210 is shown schematically in FIG. 6. Two incident beams 212 and 212' of particles, such as photons, are passed through a non-linear member 216 to produce via parametric down-conversion and sum frequency generation a set of three entangled beams 218, 220 and 221. Thus, the non-linear member 216 is capable of both parametric down-conversion and sum frequency generation. One example of such a material is lithium triborate. The beams 212 and 212' may be non-collinear or collinear as desired. Coincidence counting may be provided as described elsewhere herein.

A numerical example will illustrate the enhanced resolution obtained using this technique. Assume that the beams 212 and 212' have a wavelength of 0.5 μm. The beams 218 and 220 will have a wavelength of 1.0 μm. The beam 221 will have the same wavelength as the incident beams 212 and 212', namely 0.5 μm. However, the three beams 218, 220 and 221 will have an effective entangled wavelength of 0.25 μm, or half the wavelength and double the resolution of the incident beams 212 and 212'. Any of the beams 218, 220 and 221 could be used to observe the sample 39 described elsewhere herein. If the wavelength of a given beam 218, 220 or 221 is particularly suited to observe a certain type of material, e.g., 1.0 μm for silicon, then beams 218 or 220 may be used. Those beams 218 or 220 will provide the desirable optics wavelength with a resolution that is double that of the incident beams 212 and 212'. For a material that transmits photons more effectively at around 0.5 μm, such as silicon dioxide, the beam 221 may be used for the observation, again at double the resolution provided by the incident beams 212 and 212'. The skilled artisan will appreciate that multiple samples of the same or different materials may be simultaneously observed using, and higher orders of entanglement may be used.

While the invention may be susceptible to various modifications and alternative forms, specific embodiments have been shown by way of example in the drawings and have been described in detail herein. However, it should be understood that the invention is not intended to be limited to the particular forms disclosed Rather, the invention is to cover all modifications, equivalents and alternatives falling within the spirit and scope of the invention as defined by the following appended claims.

What is claimed is:

1. A method of inspection, comprising:
generating an entangled set of particle beams;
directing one of the entangled set of particle beams to a location of a workpiece, the one of the entangled set of particle beams interacting with the location of the workpiece; and
observing one of the entangled set of particle beams after the interaction with the location of the workpiece to inspect the location of the workpiece.

2. The method of claim 1, wherein the set comprises a pair.

3. The method of claim 1, wherein the particle beams comprise photons.

4. The method of claim 1, wherein the workpiece comprises a semiconductor substrate.

5. The method of claim 1, wherein the generating an entangled set of particle beams comprises parametric down-conversion.

6. The method of claim 5, wherein the parametric down-conversion comprises passing an incident radiation beam through a non-linear member.

7. The method of claim 6, wherein the non-linear member comprises a non-linear crystal.

8. The method of claim 7, wherein the non-linear crystal comprises N non-linearities.

9. The method of claim 1, wherein the: observing of one of the set of entangled beams comprises observing the entangled beam that interacted with the location of the workpiece.

10. The method of claim 1, wherein the observing of one of the set of entangled beams comprises observing one of the set of entangled beams that did not interact with the location of the workpiece.

11. The method of claim 1, wherein the observing of one of the set of entangled beams comprises creating an image of the location.

12. The method of claim 1, wherein the interaction with the location of the workpiece comprises reflection.

13. The method of claim 1, wherein the interaction with the location of the workpiece comprises transmission.

14. The method of claim 1, wherein information obtained form the inspection of the workpiece is used to process another workpiece.

15. The method of claim 1, wherein information obtained from the inspection of the workpiece is fed back to a process control system.

16. A method of inspection, comprising:
   generating a plurality of pairs of entangled photons, the plurality of pairs of entangled photons being divided into a first beam and a second beam;
   directing one of the first and second beams to a location of a workpiece, the one of the first and second beams interacting with the location of the workpiece; and observing one of first and second beams after the interaction with the location of the workpiece to inspect the location of the workpiece.

17. The method of claim 16, wherein the workpiece comprises a semiconductor substrate.

18. The method of claim 16, wherein the generating a plurality of pairs entangled photons comprises parametric down-conversion.

19. The method of claim 18, wherein the parametric down-conversion comprises passing an incident radiation beam through a non-linear member.

20. The method of claim 19, wherein the non-linear member comprises a non-linear crystal.

21. The method of claim 20, wherein the nonlinear crystal comprises N non-linearities.

22. The method of claim 16, wherein the observing of one of the first and second beams comprises observing the one of the first and second beams that interacted with the location of the workpiece.

23. The method of claim 16, wherein the observing of one of the first and second beams comprises observing one of the first and second beams that did not interact with the location of the workpiece.

24. The method of claim 16, wherein the observing of one of the first and second set of beams comprises creating an image of the location.

25. The method of claim 16, wherein the interaction with the location of the workpiece comprises reflection.

26. The method of claim 16, wherein the interaction with the location of the workpiece comprises transmission.

27. The method of claim 16, wherein information obtained form the inspection of the workpiece is used to process another workpiece.

28. The method of claim 16, wherein information obtained from the inspection of the workpiece is fed back to a process control system.

29. An inspection device, comprising:
   a radiation source capable of transmitting an incident beam;
   a non-linear member for producing a set of entangled beams from the incident beam;
   an imaging device for observing an interaction of one of the set of entangled beams with a location of a workpiece.

30. The inspection device of claim 29, wherein the radiation source comprises a laser.

31. The inspection device of claim 29, wherein the non-linear member comprises a non-linear crystal.

32. The inspection device of claim 31, wherein the non-linear member comprises N non-linearities.

33. The inspection device of claim 31, wherein the non-linear member comprises a plurality of cascaded non-Linear members.

34. The inspection device of claim 29, wherein the imaging device comprises a microscope.

35. The inspection device of claim 34, wherein the microscope comprises a laser scanning microscope.

36. The inspection device of claim 29, wherein the imaging device is operable to observe one of the entangled beams that physically interacts with the location of the workpiece.

37. The inspection device of claim 29, wherein the imaging device is operable to observe one of the entangled beams that does not physically interact with the location of the workpiece.

38. The inspection device of claim 29, wherein the interaction comprises reflection.

39. The inspection device of claim 29, wherein the interaction comprises transmission.

40. An inspection device, comprising:
   a radiation source capable of transmitting an incident beam;
   a non-linear crystal for producing a plurality of pairs of entangled photons from the incident beam, the plurality of pairs of entangled photons being divided into a first beam and a second beam; and
   an imaging device for observing an interaction of one of the first and second beams with a location of a semiconductor workpiece.

41. The inspection device of claim 40, wherein the radiation source comprises a laser.

42. The inspection device of claim 40, wherein the nonlinear crystal comprises N nonlinearities.

43. The inspection device of claim 40, wherein the nonlinear crystal comprises a plurality of cascaded nonlinear crystals.

44. The inspection device of claim 40, wherein the imaging device comprises a microscope.

45. The inspection device of claim 44, wherein the microscope comprises a laser scanning microscope.

46. The inspection device of claim 40, wherein the imaging device is operable to observe the one of the first and second beams that physically interacts with the Location of the workpiece.

47. The inspection device of claim 40, wherein the imaging device is operable to observe the one of the first and second beam is that does not physically interact with the location of the workpiece.

48. The inspection device of claim 40, wherein the interaction comprises reflection.

49. The inspection device of claim 40, wherein the interaction comprises transmission.

* * * * *

UNITED STATES PATENT AND TRADEMARK OFFICE
CERTIFICATE OF CORRECTION

PATENT NO. : 6,714,294 B1 Page 1 of 1
DATED : March 30, 2004
INVENTOR(S) : Michael R. Bruce et al.

It is certified that error appears in the above-identified patent and that said Letters Patent is hereby corrected as shown below:

Column 2,
Line 60, delete "A" and substitute -- $\lambda$ --.

Column 3,
Line 8, delete the second occurrence of "a" and substitute -- $2\lambda$ --.

Column 8,
Line 49, delete "beam is" and substitute -- beams --.

Signed and Sealed this

Twenty-fifth Day of May, 2004

JON W. DUDAS
*Acting Director of the United States Patent and Trademark Office*